United States Patent [19]
Goux

[11] Patent Number: 5,227,296
[45] Date of Patent: Jul. 13, 1993

[54] ENZYMATIC SYNTHESIS OF ISOTOPICALLY LABELED CARBOHYDRATES, NUCLEOTIDES AND CITRIC ACID INTERMEDIATES

[75] Inventor: Warren J. Goux, Farmers Branch, Tex.

[73] Assignee: Board of Regents, The University of Texas System, Austin, Tex.

[21] Appl. No.: 587,934

[22] Filed: Sep. 25, 1990

[51] Int. Cl.$^5$ .................. C12P 13/04; C12P 13/14; C12P 7/50

[52] U.S. Cl. .................. 435/110; 435/72; 435/106; 435/115; 435/143

[58] Field of Search ............ 435/106, 115, 110, 143, 435/72

[56] References Cited

U.S. PATENT DOCUMENTS

| | | | |
|---|---|---|---|
| 4,656,133 | 4/1987 | Goux | 435/72 |
| 4,826,766 | 5/1989 | Rozzell | 435/106 |
| 4,880,738 | 11/1989 | Rozzell | 435/106 |

FOREIGN PATENT DOCUMENTS 0202094 11/1986 European Pat. Off. .
157107 10/1982 German Democratic Rep. .

OTHER PUBLICATIONS

Chenault, H. Keith et al., "Regeneration of Nicotinamide Cofactors for use in Organic Synthesis," Applied Biochemistry & Biotechnology, 14:147–197, 1987.
Webb, E. L., "Enzyme Nomenclature 1984," Academic Press, Orlando (US), pp. 222–223, 1984.
Webb, Edwin C., "Enzyme Nomenclature 1984," Recommendations of the Nomenclature Committee of the International Union of Biochemistry on the Nomenclature and Classification of Enzyme-Catalysed Reactions, Academic Press, 1984.
International Search Report, Mar. 19, 1992.
Article by Barker and Serianni, "Carbohydrates in Solution: Studies With Stable Isotopes", Acc. Chem. Res., vol. 19, pp. 307–313, 1986.
Article by Serianni et al., "Chemical Synthesis of Monosaccharides Enriched With Carbon Isotopes", Methods in Enzymology, vol. 89, pp. 64–73.
Article by Serianni and Barker, "Synthetic Approaches to Carbohydrates Enriched With Stable Isotopes of Carbon, Hydrogen and Oxygen", Isotopes in the Physical and Biomedical Sciences, vol. 1, Labelled Compounds (Part A), Chapter 8, pp. 211–236, 1987.
Article by Angyal et al., "Selective Deuteration Over Raney-Nickel In Deuterium Oxide: Methyl Glycosides", Carbohydrate Research, vol. 157 pp. 83–94, 1986.
Article by Clark, Jr. and Barker, "General Methods for Enriching Aldoses With Oxygen Isotopes", Carbohydrate Research, vol. 153, pp. 253–261, 1986.
Article by Bhattacharjee et al., "Hydride Reduction of Aldonolactones to Aldoses", Carbohydrate Research vol. 42, pp. 259–266, 1975.
Article by Kim et al., "Enzymes in Carbohydrate Synthesis: N-Acetylneuraminic Acid Aldolase Catalyzed Reactions and Preparation of N-Acetyl-2-deoxy-D-neuraminic Acid Derivatives", J. Am. Chem. Soc., vol. 110, pp. 6481–6486, 1988.
Article by Bednarski et al., "Rabbit Muscle Aldolase as a Catalyst in Organic Synthesis", J. Am. Chem. Soc., vol. 111, No. 2, pp. 627–635, 1989.
Article by Durrwachter and Wong, "Fructose 1,6-Diphosphate Aldolase Catalyzed Stereoselective Synthesis of C-Alkyl and N-Containing Sugars: Thermodynamically Controlled C—C Bond Formations", J. Org. Chem., vol. 53, No. 18, pp. 4175–4181, 1988.

Primary Examiner—Herbert J. Lilling
Attorney, Agent, or Firm—Arnold, White & Durkee

[57] ABSTRACT

The present invention relates to a general method of enzymatic synthesis of isotopically labeled carbohydrates, sugars and nucleosides. Labeled citric acid cycle intermediates, amino acids and ribose mononucleotides may be rapidly and conveniently synthesized from labeled pyruvate, lactate or L-alanine. The method employs a novel nicotinamide dinucleotide regeneration system which permits use of low NADH levels. The method may be manipulated to allow labeling at a variety of carbon/hydrogen sites.

4 Claims, 1 Drawing Sheet

OTHER PUBLICATIONS

Article by Wong and Whitesides, "Synthesis of Sugars by Aldolase-Catalyzed Condensation Reactions", J. Org. Chem., vol. 48, No. 19, pp. 3199–3205, 1983.

Article by Bednarski et al., "Aldolase-Catalyzed Synthesis of Complex $C_8$ and $C_9$ Monosaccharides", Tetrahedron Letters, vol. 27, No. 48, pp. 5807–5810, 1986.

Article by Borysenko et al., "Synthesis of Aldose Sugars from Half-Protected Dialdehydes Using Rabbit Muscle Aldolase", J. Am. Chem. Soc., vol. 111, pp. 9275–9276, 1989.

Article by Durrwachter et al., "Enzymatic Aldol Condensation/Isomerization as a Route to Unusual Sugar Derivatives", J. Am. Chem. Soc., vol. 108, No. 24, pp. 7812–7818, 1986.

Article by Goux, "Enzymic synthesis of $^{13}$C-labeled ketose phosphates from three-carbon precursors. Specific assignment of resonances in $^{13}$C-n.m.r. spectra of D-fructose 1,6-diphosphate", Carbohydrate Research, vol. 122, pp. 332–339, 1983.

Article by Kerr and Ott, "Preparation of D- and L-Alanine-2,3-$^{13}C_2$", J. of Labelled Compounds and Radiopharmaceuticals, vol. XV, pp. 503–509, Oct., 1978.

Article by Kendall and McKensie, "dl-$\beta$-Phenylalanine", Org. Syn. Coll., vol. 2, pp. 491–494, 1943.

Article by Loftfield and Eigner, "The Preparation of Pure [I-$^{14}$C]- and [I-$^{3}$H]-Labeled L-Amino Acids", Biochim. Biophys. Acta, vol. 130, pp. 449–457, 1966.

Article by Berger et al., "A New Method for the Synthesis of Optically Active $\alpha$-Amino Acids and Their $N^a$ Derivatives via Acylamino Malonates", J. Org. Chem., vol. 38, No. 3, pp. 457–460, 1973.

Article by Baddiley et al., "A Synthesis of Alanine Labeled With Heavy Carbon In the $\alpha$ Position", J. Biol. Chem., vol. 178, pp. 399–402, 1949.

Article by Fryzuk and Bosnich, "Asymmetric Synthesis. Production of Optically Active Amino Acids by Catalytic Hydrogenation", J. of Am. Chem. Soc., vol. 99, No. 19, pp. 6262–6267, Sep. 14, 1977.

Article by Giza and Ressler, "Synthesis of L-$\beta$-Cyanoalanine-4-$^{14}$C, L-Asparagine-4-$^{14}$C, and L-Aspartic Acid-4-$^{14}$C", J. of Labelled Compounds, vol. V, No. 2, pp. 142–151, Apr.–Jun., 1969.

Article by Havránek et al., "Synthesis of L-Glutamine-5-$^{14}$C, L-Glutamic Acid-5-$^{14}$C, and L-Ornithine-5-$^{14}$C", J. of Labelled Compounds, vol. VI, No. 4, pp. 345–354, Oct.–Dec. 1970.

Article by LeMaster and Cronan, Jr., "Biosynthetic Production of $^{13}$C-Labeled Amino Acids with Site-Specific Enrichment", J. of Bio. Chem., vol. 257, No. 3, pp. 1224–1230, 1982.

Article by Ott, "Synthesis with Stable Isotopes of Carbon, Nitrogen and Oxygen", John Wiley, New York, N.Y., pp. 63–66, 1982.

Article by Baldwin et al., "Application of *E. coli* Aspartate Transaminase to Amino Acid Synthesis", Tetrahedron Letters, vol. 28, No. 32, pp. 3745–3746, 1987.

Article by Wood et al., "Acyl-Enzyme Exchange Detection by Intermolecular Oxygen Scrambling: An Application of the $^{18}$O-Isotope Effect in $^{13}$C NMR", J. Am. Chem. Soc., vol. 106, pp. 2222–2223, 1984.

Article by Malloy et al., "Evaluation of Carbon Flux and Substrate Selection Through Alternate Pathways Involving the Citric Acid Cycle of the Heart by $^{13}$C NMR Spectroscopy", J. of Biol. Chem., vol. 263, No. 15, pp. 6964–6971, 1988.

Article by Katz et al., "Studies of Glycogen Synthesis and the Krebs Cycle by Mass Isotopomer Analysis with [U-$^{13}$C]Glucose in Rats", J. of Biol. Chem., vol. 264, No. 22, pp. 12994–13001, 1989.

Article by Shulman et al., "Nuclear Magnetic Resonance Spectroscopy in Diagnostic and Investigative Medicine", J. Clin. Invest., vol. 74, pp. 1127–1131, Oct. 1984.

Article by Kazlauskas and Whitesides, "Synthesis of Methoxycarbonyl Phosphate, a New Reagent Having High Phosphoryl Donor Potential for Use in ATP Cofactor Regeneration", J. Org. Chem., vol. 50, No. 7, pp. 1069–1076, 1985.

Article by Hirschbein et al., "Synthesis of Phosphoenolpyruvate and Its Use in Adenosine Triphosphate Cofactor Regeneration", J. Org. Chem., vol. 47, pp. 3765–3766, 1982.

Article by Crans and Whitesides, "A convenient Synthesis of Disodium Acetyl Phosphate for Use in in Situ ATP Cofactor Regeneration", J. Org. Chem., vol. 48, No. 18, pp. 3130–3132, 1983.

Article by Simon et al., "Convenient Synthesis of Cytidine 5'-Triphosphate, Guanosine 5'-Triphosphate, and Uridine 5'-Triphosphate and Their Use in the Preparation of UDP-glucose, UDP-glucuronic Acid, and GDP-Mannose", J. Org. Chem., vol. 55, No. 6, pp. 1834–1841, 1990.

OTHER PUBLICATIONS

Article by Wong and Whitesides, "Enzyme-Catalyzed Organic Synthesis: NAD(P)H Cofactor Regneration by Using Glucose 6-Phosphate and the Glucose-6-phosphate Dehydrogenase from *Leuconostoc mesenteroides*", J. Am. Chem., vol. 103, pp. 4890–4899, 1981.

Article by Hartman, "Isolation and Characterization of an Active-Site Peptide from Triose Phosphate Isomerase", J. Am. Chem. Soc., vol. 92, No. 7, pp. 2170–2172, 1970.

Article by Gross et al., "Practical Synthesis of 5-Phospho-D-ribosyl α-1-Pyrophosphate (PRPP): Enzymatic Routes from Ribose 5-Phosphate or Ribose", Am. Chem. Soc., vol. 105, No. 25, pp. 7428–7435, 1983.

Article by Walt et al., "An Efficient Chemical and Enzymatic Synthesis of Nicotinamide Adenine Dinucleotide (NAD+)", J. Am. Chem. Soc., vol. 106, pp. 234–239, 1984.

Article by Lee and Whitesides, "Enzyme-Catalyzed Organice Synthesis: A Comparison of Strategies for in Situ Regeneration of NAD from NADH", J. Am. Chem. Soc., vol. 107, pp. 6999–7008, 1985.

Article by Ott, "Synthesis with Stable Isotopes", John Wiley, N.Y., New York, p. 47, 1981.

Article by Ennor and Stocken, "Sodium Phosphocreatine", in *Biochemical Preparations*, vol. 5, pp. 9–12.

Article by Fansler and Lowenstein, "Aconitase from Pig Heart", in Methods Enzymology, vol. 13, pp. 26–30, 1969.

Article by Wong et al., "Enzymes in Organic Synthesis: Use of Subtilisin and a Highly Stable Mutant Derived from Multiple Site-Specific Mutations", J. Am. Chem. Soc., vol. 112, pp. 945-953, 1990.

Article by Ozaki et al., "Overproduction and Substrate Specificity of a Bacterial Fuculose-1-phosphate Aldolase: A New Enzymatic Catalyst for Stereocontrolled Aldol Condensation", J. Am. Chem. Soc., vol. 112, pp. 4970–4971, 1990.

Article by Margolis and Coxon, "Identification and Quantitation of the Impurities in Sodium Pyruvate", Anal. Chem., vol. 58, pp. 2504–2510, 1986.

Article by Hartman, "Haloacetol Phophates. Characterization of the Active Site of Rabbit Muscle Triose Phosphate Isomerase", Biochem., vol. 10, No. 1, pp. 146–154, 1971.

Article by Serianni et al., "Cyanohydrin Synthesis: Studies with [$^{13}$C]Cyanide", J. Org. Chem., vol. 45, pp. 3329–3341, 1980.

Article by Whitesides and Wong, "Enzymes as Catalysts in Organic Synthesis", Aldrichimica Acta, vol. 16, No. 2, pp. 27–35, 1983.

Article by Shaked and Whitesides, "Enzyme-Catalyzed Organice Synthesis: NADH Regeneration by Using Formate Dehydrogenase", J. Am. Chem. Soc., vol. 102, pp. 7104–7105, 1980.

Article by Pollak et al., "Enzyme Immobilization by Condensation Copolymerization into Cross-Linked Polyacrylamide Gels", J. Am. Chem. Soc., vol. 102, pp. 6324–6336, 1980.

Article by Bolte and Whitesides, "Enzymatic Synthesis of Arginine Phosphate with Coupled ATP Cofactor Regeneration", Bioorg. Chem., vol. 12, pp. 170–175, 1984.

Article by Effenberger and Straub, "A Novel Convenient Preparation of Dihydroxyacetone Phosphate and Its Use in Enzymatic Aldol Reactions", Tetrahedron Letters, vol. 28, No. 15, pp. 1641–1644, 1987.

Article by Straub et al., "Aldolase-Catalyzed C-C Bond Formation for Stereoselective Synthesis of Nitrogen-Containing Carbohydrates", J. Org. Chem., vol. 55, pp. 3926–3932, 1990.

Article by Crans and Whitesides, "Glycerol Kinase: Substrate Specificity", J. Am. Chem. Soc., vol. 107, pp. 7008–7018, 1985.

Article by Nejedly et al., "Efficient Enzymatic Synthesis of Adenine-Labelled ATP in One-Step Procedure", Radiochem. Radioanal. Letters, vol. 53, Nos. 5–6, pp. 329–342, 1982.

# ENZYMATIC SYNTHESIS OF ISOTOPICALLY LABELED CARBOHYDRATES, NUCLEOTIDES AND CITRIC ACID INTERMEDIATES

BACKGROUND OF THE INVENTION

1. Field of the Invention

The invention is a method of enzymatic synthesis of isotopically labeled metabolites. In particular, the invention relates to a rapid and convenient synthesis of isotopically labeled carbohydrates, citric acid cycle intermediates, amino acids and ribose mononucleotides, all of which may be derived from labeled pyruvate, lactate or L-alanine.

2. Description of Related Art

Methods of preparing sugars and nucleotides labeled in the carbohydrate moiety have traditionally utilized the reactions of classic organic chemistry, (1-3). Typically, an aldose is prepared labeled at the anomeric carbon (C-1) by condensing an aldose one carbon shorter with isotopically labeled cyanide for the preparation of carbon-13 or carbon-14 labeled sugars. Deuterium, tritium or oxygen labeled isotopes may be prepared by subsequent reduction with hydrogen isotope in the presence of isotopically enriched aqueous solution, (4-6). Using this reaction sequence, a mixture of C-2 epimers is obtained, which then must be separated by chromatography. Yields of the desired product are usually in the range of 40-80%. Labeling at C-2 may be achieved by a molybdate ion catalyzed epimerization followed by chromatography. In order to label carbon sites other than C-1 or C-2, the entire sequence of reactions must be repeated, using the appropriately labeled material during one of the turns of the cycle. Not unexpectedly, each turn of such a cycle severely diminishes the yield of the desired product.

Labeling at internal carbon sites of a carbohydrate is best accomplished by enzymatic routes. Due to the permissive nature of rabbit muscle aldolase to accept a range of three to six carbon aldehydes, a variety of labeled sugar phosphates can be prepared enzymatically if the appropriately labeled substrate is provided (7-13). The labeled substrate is prepared by a chemical method, such as those described above, or enzymatically prepared from glycerol. In general, synthesis of these precursors may require several steps.

An improved method of isotopically labeled carbohydrate synthesis using enzymes of the glycolytic pathway provides good yields of hexose and pentose sugars and the various phosphorylated intermediates leading to these sugars (14,15). This method is essentially a single step reaction requiring mixing labeled pyruvate with enzymes of the glycolytic and neoglycolytic pathway and allowing the reaction to proceed to completion. Although this method provides a simple and rapid synthesis, high levels of ATP and NADH are required to force the reaction to completion and the final product requires a time-consuming chromatographic separation.

No general chemical procedure for the isotopic labeling of L-amino acids exists. Methods have been described for preparing [2,3-$^{13}$C] DL-alanine (16), [1-$^{13}$C] DL-alanine (17-19), [2-$^{13}$C] DL-alanine (20) and for the asymmetric synthesis of unlabeled L-alanine (21). The latter method, however, is difficult to adapt to an isotopically enriched synthetic scheme because of the difficulty in preparing the labeled starting material, α-acetamidoacrylic acid. Methods used for preparing [1-$^{13}$C] DL-alanine have also been used to prepare racemic mixtures of other amino acids labeled at the carbonyl carbons. Methods also exist for the isotopic labeling of aspartic and glutamic acids at their side chain carboxyls (22-23). More recently, methods have become available for isolating amino acids from bacteria grown on $^{13}$C-labeled substrates. Selection of mutant strains allows the possibility of site specific labeling patterns (24).

The above classical chemical methods suffer because they only allow for a few simple labeling patterns and because a racemic mixture of products is obtained, ultimately decreasing the overall yield of the desired enantiomer. The bacterial method, while of greater overall utility, requires knowledge of the isolation of amino acids from hydrolyzed proteins.

Of the citric acid cycle intermediates, [2, 3, 2-$^{13}$C$_2$] succinate has been synthesized by classical methods from diethylmalonate and 2-$^{13}$C-ethylchloroacetate while [1,4-$^{13}$C$_2$] and [2,3-$^{13}$C$_2$] succinate have been prepared from $^{13}$C-enriched potassium cyanide and/or [1,2-$^{13}$C]1,2-dibromoethane (25). Using the first of these two chemical methods, the product can be labeled at any chosen position. However, the difficulty in obtaining $^{13}$C-labeled malonic acid may make the method less than desirable. The second of the two methods is useful only for labeling of the two carboxyl carbons or the two internal carbons.

[1-$^{13}$C] or [4-$^{13}$C] malate can be prepared from the appropriately labeled aspartic acid using chemical methods (25). Similarly the reaction has been carried out enzymatically using an aspartate transaminase catalyzed reaction (26). Both methods have the disadvantage of requiring the appropriately labeled aspartic acid substrate.

[5-$^{13}$C, $^{18}$O] citrate has been prepared enzymatically from [1-$^{13}$C] acetate and unlabeled oxaloacetate (27). No convenient chemical synthesis of isotopically labeled citrate exists.

Isotopically labeled products are of increasing value in biochemical and medical research. Already analysis of metabolic disposition by nuclear magnetic resonance techniques has been used to monitor normal and pathological metabolism (28-30). Deuterated and perhaps $^{13}$C isoptopically labeled compounds may also have clinical applications in magnetic resonance imaging.

With these ever-increasing medical and clinical applications, there is a need for adequate and reliable supplies of labeled compounds particularly suited for safe use in humans. With attention turning to new techniques capable of detecting labeled metabolites and intermediates associated with metabolic processes, there is increased pressure to develop rapid and efficient methods of obtaining labeled compounds suitable for metabolic diagnosis, including citric acid cycle intermediates, carbohydrates and nucleotides. Methods which do not require time consuming isolation procedures, involve simple purification and are adaptable in providing a wide selection of labeled compounds would alleviate some of the problems associated with presently available methods of obtaining these labeled compounds.

SUMMARY OF THE INVENTION

A general scheme of the present invention is summarized below.

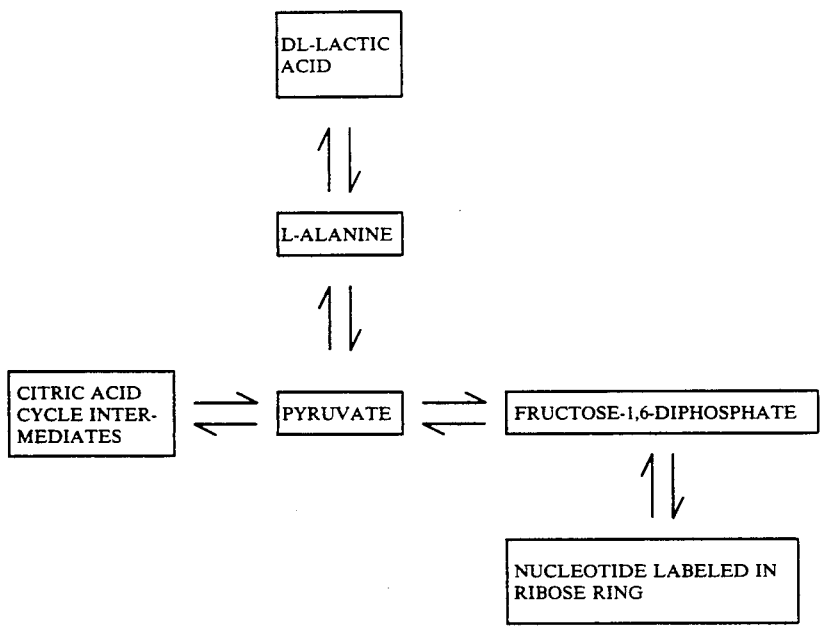

The enzymatic synthesis of fructose 1,6-diphosphate (FDP) from isotopically labeled pyruvate differs from a previously proposed synthesis (14) in: using a commercially available enzyme, pyruvate kinase, in the initial conversion of isotopically labeled pyruvate to phosphoenolpyruvate; employing a novel NAD regeneration system in order to avoid high NADH levels; maximizing the efficiency of the conversion of isotopically labeled pyruvate to FDP by minimizing the amounts of the enzymes needed and taking measures to preserve enzyme activity; specifically allowing for the inactivation of TPI, so that FDP is isotopically labeled only at carbon sites 4-6; presenting a formulation which allows preparation of isotopically labeled nucleotides from FDP, allowing for the preparation of FDP from isotopically labeled L-alanine.

In addition, the present invention particularly addresses the enzymatic preparation of labeled citric acid cycle intermediates, α-ketoglutarate, oxaloacetate, malate, fumarate, citrate and isocitrate from labeled L-alanine, pyruvate and acetate. The method can be manipulated to allow labeling at a variety of carbon/hydrogen sites.

Transamination of oxaloacetate or α-ketoglutarate allows preparation of isotopically labeled aspartate and glutamate.

One general aspect of the invention is the enzymatic synthesis of a labeled carbohydrate. The synthesis involves the steps of preparing a reaction mixture which contains an adenosine phosphate regeneration system, a nicotinamide adenine dinucleotide regeneration system and a labeled pyruvate. To this reaction mixture is added an enzyme combination mixture containing pyruvate kinase, enolase, phosphoglycerate mutase, phosphoglycerate kinase, glyceraldehyde-3-phosphate dehydrogenase, and aldolase. The entire reaction mixture is incubated together and the labeled carbohydrate is obtained from the reaction mixture.

The adenosine phosphate regeneration system is preferably composed of phosphocreatine, phosphocreatine phosphokinase and an adenosine phosphate. This adenosine phosphate may be ATP, but ADP may also be used, recognizing that ATP will be generated, utilized and then recycled to form ATP from the ADP. The amount of adenosine phosphate added to the system generally ranges from about 2% to 5% of the amount of phosphocreatine added, but other amounts are not excluded so long as the amount is sufficient to allow the reaction to proceed at a reasonable rate.

The nicotinamide adenine dinucleotide regeneration system will typically include a reducing sugar, a nicotinamide adenine dinucleotide and a reducing sugar dehydrogenase. The nicotinamide adenine dinucleotide is preferably NADH. The amount of nicotinamide adenine dinucleotide added to the system will generally range from about 2% to 5% of the level of the glucose or other reducing sugar added, but other amounts are not excluded so long as a reasonable rate of reaction can be maintained.

Prior to running the reaction, a triose phosphate isomerase inhibitor may be added to the enzyme mixture. For example, any of the 3-haloacetol phosphates are suitable inhibitors. The amount of isomerase inhibitor added is usually about a two-fold molar excess with respect to the total enzyme concentration. A larger excess, approximately ten-fold, should be avoided because of the potential to inhibit enzymes required for the synthesis. Any excess inhibitor present in the reaction mixture may be removed after the inhibitor reacts with the triose phosphate isomerase.

The reaction may be conducted under any nonoxidizing atmosphere, typically an inert gas including argon, nitrogen, xenon or helium. Yields are often improved under these conditions because air oxidation becomes less of a factor. This may be particularly important in preventing the oxidation of the enzymes used in the reaction. The reaction is preferably incubated at a pH between about 6.7 and 7.5, although this pH range is not intended to be limiting.

At the end of the reaction, the enzymes may be removed from the reaction mixture by any method that will effectively separate enzymes from the compounds used in the reaction mixture. This will ordinarily be by ultrafiltration, but dialysis could also be employed. Excess phosphocreatine may be removed from the reaction mixture by hydrolysis but this is not necessary. The labeled product, fructose-1,6-diphosphate, is preferably obtained directly by precipitation from the reaction mixture as a heavy metal salt. A calcium salt is preferred although other similar heavy metal salts will also work, for example, barium.

In another aspect of the invention, a labeled carbohydrate may be prepared from labeled alanine. First a solution is prepared containing an adenosine phosphate regeneration system, a nicotinamide adenine dinucleotide regeneration system, α-ketoglutarate and the labeled alanine. To this solution is added a mixture of enzymes, generally including those that will serve the function of a pyruvate kinase, enolase, phosphoglycerate mutase, phosphoglycerate kinase, glyceraldehyde-3-phosphate dehydrogenase, aldolase, and pyruvate glutamate transaminase. The mixture is incubated and labeled carbohydrate may be obtained from the reaction mixture by precipitation as a heavy metal salt, preferably as a $Ca^{2+}$ salt. The adenosine phosphate regeneration system and nicotinamide adenine dinucleotide regeneration system are the same as described previously.

Labeled L-alanine may also be obtained using the method of the present invention. In this synthesis, DL-lactate, α-ketoglutarate, NAD and labeled pyruvate are incubated with L-lactate dehydrogenase, D-lactate dehydrogenase, glutamate dehydrogenase and pyruvate-alanine transaminase. The amount of time allowed for the reaction is sufficient to allow formation of labeled L-alanine. Labeled L-alanine may then be isolated using any of a number of methods suitable for amino acid isolation, for example, chromatography.

Phosphocreatine may be also prepared using the method of the present invention. One method of preparation is to incubate together creatine, creatine phosphokinase and an adenosine triphosphate regeneration system, one such system being phosphoenol pyruvate and pyruvate kinase. A second system makes use of the glycolytic pathway to regenerate ATP from glucose. To this system are added pyruvate, hexokinase phosphoglucose isomerase, phosphofructokinase, aldolase, phosphoglycerate mutase, L-lactate dehydrogenase, pyruvate kinase, enolase, glyceraldehyde phosphate dehydrogenase and an NADH regeneration system. The phosphocreatine may be obtained by precipitation as a heavy metal salt, preferably as the barium salt. Yields are increased if the reaction is run in an inert atmosphere such as nitrogen, argon, or helium.

In another aspect of the invention, labeled pyruvate is converted to labeled aspartate by incubating labeled pyruvate with pyruvate carboxylase, glutamic-oxaloacetic transaminase, glutamate and an ATP regenerating system. Incubation is continued until labeled aspartate is formed. The product may be isolated by any of a number of methods, including chromatography, for example, high performance liquid chromatography.

Generally, the invention allows the convenient preparation of several amino acids and citric acid cycle intermediates. One simply incubates a labeled precursor of a citric acid cycle intermediate with one or more enzymes capable of converting the precursor into the intermediate. Labeled malate, citrate, isocitrate, α-ketoglutarate, alanine, glutamate and aspartate are particular examples of labeled compounds that can be prepared.

Malate may be enzymatically synthesized by at least three methods. In one method, labeled pyruvate is incubated with malic enzyme, and an NADPH regenerating system in the presence of a source of carbon dioxide, for example bicarbonate, until labeled malate is formed. In a second method, labeled pyruvate, an ATP regenerating system, and an NADH regenerating system, pyruvate carboxylase and malic dehydrogenase are incubated together until labeled malate is formed. In a third method, labeled pyruvate, an ATP regenerating system, and an NADH regenerating system are incubated with phosphoenolpyruvate carboxylase, malic dehydrogenase and pyruvate kinase for a period of time sufficient to allow formation of labeled malate. Labeled malate formed may be isolated from the reaction mixture by any of a number of methods, including high performance liquid chromatography.

Labeled citrate may be prepared by incubating labeled or unlabeled acetate, labeled or unlabeled pyruvate, a labeled or unlabeled source of $CO_2$ such as bicarbonate, an ATP regenerating system, reduced coenzyme A, citrate synthetase, pyruvate carboxylase, myokinase and acetyl coenzyme A synthetase.

Labeled isocitrate may be prepared by incubating the mixture used to prepare labeled citrate with the addition of aconitase.

In yet another aspect of the invention, labeled α-ketoglutarate, labeled alanine and labeled glutamate may be prepared by incubating ammonium ion and labeled citrate with isocitrate dehydrogenase, aconitase, glutamate dehydrogenase and glutamate pyruvate transaminase. The mixture of labeled α-ketoglutarate, labeled alanine, labeled glutamate and labeled pyruvate may be separated by chromatography, preferably anion exchange chromatography.

DETAILED DESCRIPTION OF PREFERRED EMBODIMENTS

Figure 1:
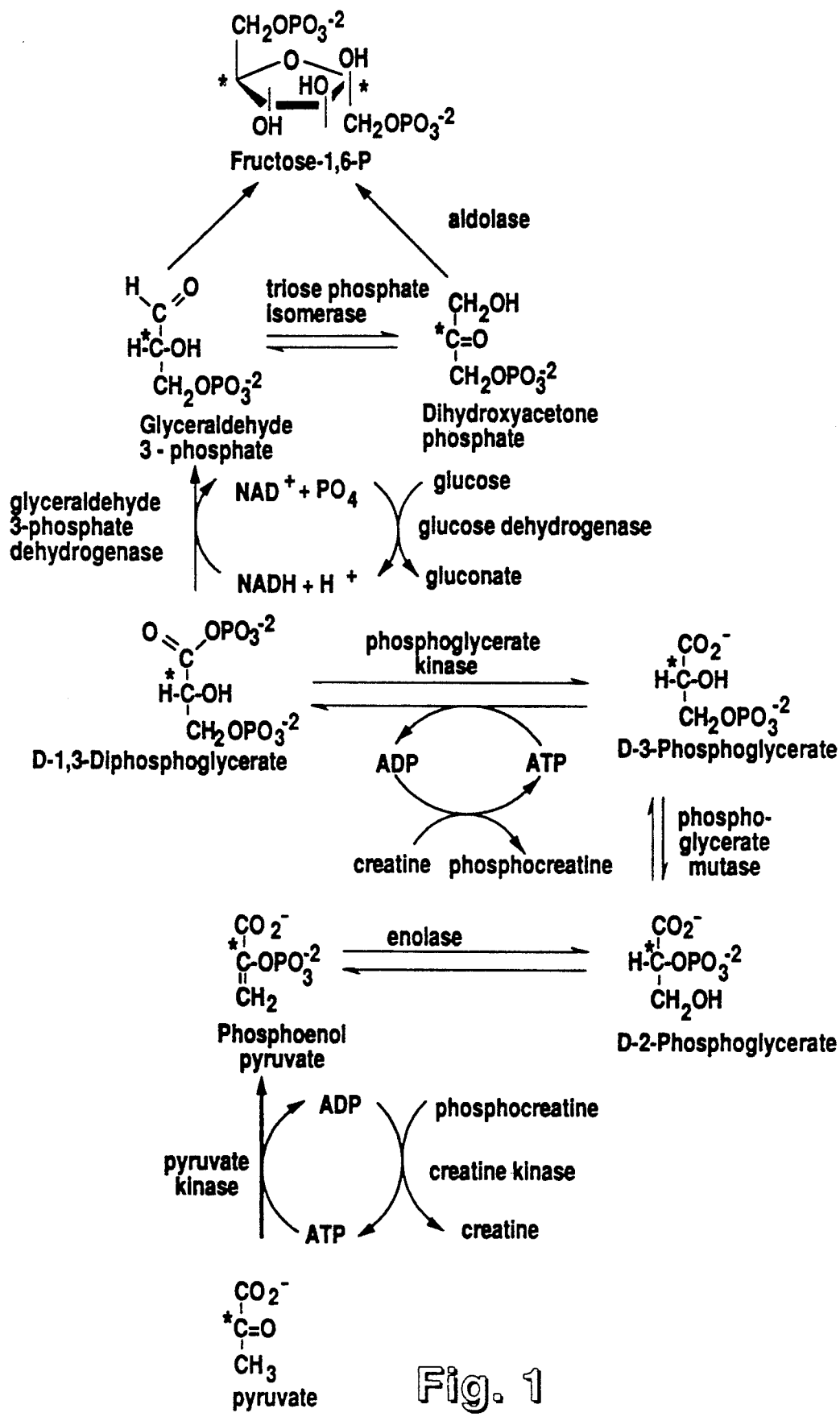
FIG. 1 is a diagram showing a synthetic scheme for the preparation of $[2,5-^{13}C_2]$fructose diphosphate (FDP) from $[2-^{13}C]$pyruvate.

One aspect of the present invention is a method of enzymatic synthesis of labeled carbohydrates from isotopically labeled pyruvate using the enzymes of the glycolytic pathway. This is illustrated diagrammatically in FIG. 1. The overall scheme differs from that described previously (14) in at least one respect which includes novel nucleotide regeneration systems. With such systems, commercially available enzymes may be used, often obtainable at nominal cost.

As was the case in a previous invention (14), an ATP regeneration system based on the transfer of phosphate from phosphocreatine to ATP is used. However, in the present invention the level of ATP added to the reaction mixture is generally at least 30-fold less than the level of pyruvate added while in a previously described method, the amount of ATP added to the reaction mixture was twice the amount of pyruvate added. At the higher concentrations, ATP is an inhibitor of pyruvate kinase. At concentrations used previously, the overall reaction became so slow as to preclude the use of commercially available pyruvate kinase. The present embodiment does not preclude the use of other ATP regenerating systems (31-34) as long as one member of the phosphorylated donor/dephosphorylated donor pair does not occur as an intermediate, product or reactant in the overall synthetic scheme.

A novel NADH regeneration system is employed based on the glucose/gluconate redox pair. Without this regeneration system, the overall equilibria of the reaction would lie in favor of reactants, and again prohibit the use of pyruvate kinase. The ATP and NADH regeneration systems are shown below.

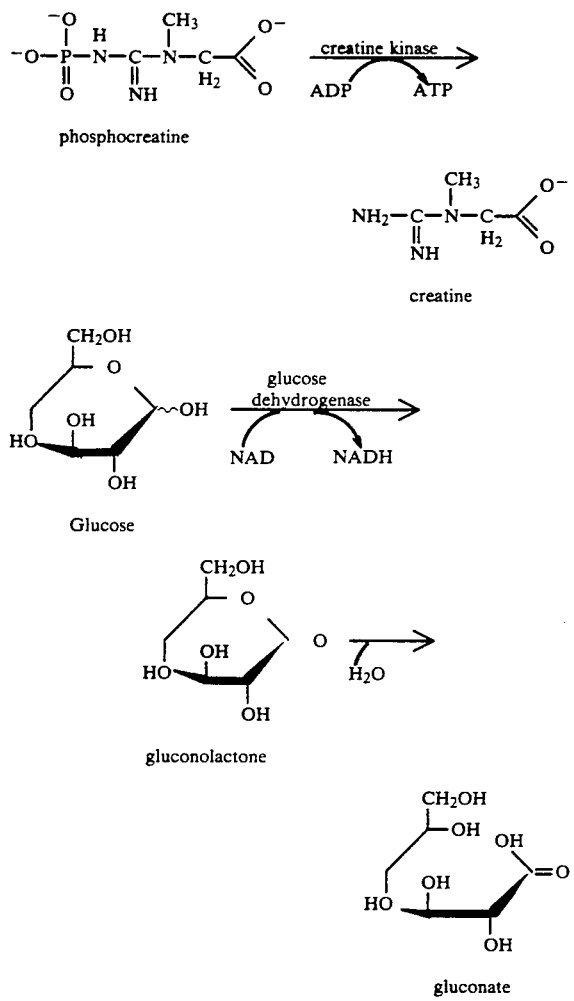

Synthesis of Labeled Fructose Diphosphate From Pyruvate or L-Alanine

The synthesis of labeled fructose diphosphate from labeled pyruvate has been described previously and to the extent that there exists similarities in technical procedure, the previous description is hereby incorporated by reference (14).

In the present invention NADH is regenerated in situ by adding glucose and glucose dehydrogenase to the reaction mixture. The ATP regeneration system is the same as that previously described (14–15). NADH oxidation to NAD during conversion of 1,3-diphosphoglycerate to glyceraldehyde 3-phosphate is coupled to the oxidation of glucose by glucose dehydrogenase reduction of NAD+ to NADH. It is therefore necessary to add only small quantities of either NAD+ or NADH initially to the reaction mixture. Glucose/glucose dehydrogenase is a preferred system for the coupled reduction of NAD+ in the synthesis of phosphorylated sugars, since both glucose and gluconate are easily separated from the final reaction mixture. However, this particular NADH regenerating system is not intended to be limiting. Any couple, for example, another reducing sugar and its dehydrogenase, could work provided the oxidation potential is in a range that will promote efficient reduction of NAD+ but not reduction of other components of the reaction mixture (35).

In preferred aspects of the invention, enzymes, labeled substrate starting material and components of the ATP and NADH regenerating system are mixed and allowed to react until the product is formed The enzymes are removed from the reaction mixture, usually by ultrafiltration. One of the problems previously encountered with carbohydrate synthesis by this method has been isolation of the product carbohydrate, requiring chromatographic separation. The advantage of the present invention is that the product, a sugar phosphate, can be precipitated as a heavy metal phosphate salt.

One of the problems in preparing [4-$^{13}$C], [5-$^{13}$C] and [6-$^{13}$C] fructose-1,6-diphosphate from [1-$^{13}$C], [2-$^{13}$C] and [3-$^{13}$C] pyruvate using purchased enzymes is that triose phosphate isomerase is a commonly found contaminant. This problem is solved in the present invention by incubating the enzyme combination to be used in the reaction with a specific irreversible triose phosphate isomerase inhibitor at a relatively low molar ratio with respect to the total enzyme concentration (36). Enzymes other than triose phosphate isomerase will retain their activity. In a preferred embodiment, excess inhibitor is dialyzed away prior to addition of enzymes to the reaction mixture. This is not intended to exclude using the enzymes without dialysis, and in large scale operations, it may be advantageous to titrate aliquots of the soluble enzyme mixture in order to add inhibitor sufficient to just inactivate the triose phosphate isomerase, thereby eliminating the dialysis step.

In another embodiment of the present method of preparing a labeled carbohydrate, labeled L-alanine is converted to a labeled carbohydrate. In this reaction, the starting material is labeled alanine which is converted in situ to pyruvate (see below) by the action of the enzyme pyruvate-alanine transaminase. This conversion exemplifies the versatility of the invention.

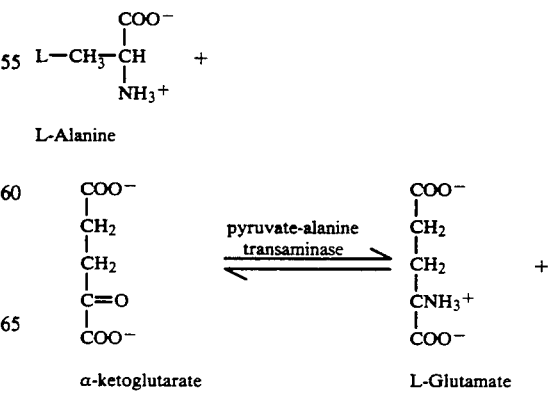

Preparation of Labeled Ribonucleotides

The preparation of nucleotides and nicotinamide adenine dinucleotides are also contemplated to be within the scope of the present invention. In the first step of the sequence, $^{13}$C-labeled FDP is prepared from

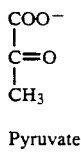

Pyruvate catalyzed reaction followed by reduction in a malate dehydrogenase catalyzed reaction. The ATP used in the reaction is regenerated using any one of the available ATP regenerating systems (31-34). An equilibrium mixture of fumarate and malate may also be formed by including fumarase in the reaction mixture. However, the specific nature of the labeling patterns are lost due to the symmetry of the fumarate molecule. If α-ketoglutarate is included in the reaction mixture, one may use isotopically labeled L-alanine as a starting material rather than pyruvate, in the manner previously described for the reverse glycolysis reaction. Preparation of malate, fumarate and oxaloacetate is indicated below.

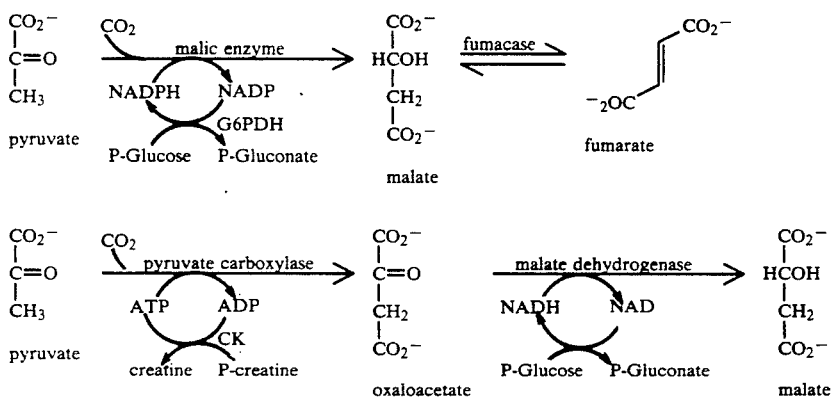

labeled pyruvate or L-alanine according to the reverse glycolysis scheme. The product is then converted to fructose-6-phosphate either chemically, by acid hydrolysis, or enzymatically, using fructose-1,6-diphosphatase. Glucose-6-phosphate is then formed by addition of phosphoglucose isomerase to the reaction mixture. D-ribose-5-phosphate (and D-ribulose-5-phosphate) are then formed by subsequently adding the commercially available enzymes of the phosphogluconate pathway (14-15). In the sequence of reactions NADP is regenerated in the manner discussed previously. Phosphoribosyl pyrophosphate and nucleotides may then be prepared using known enzymatic methods (37-39).

Preparation of Labeled Citric Acid Cycle Intermediates

In yet another embodiment, isotopically labeled citric acid cycle intermediates may be prepared from labeled bicarbonate, pyruvate, L-alanine and acetic acid. For example, malic enzyme can be used to reduce and carboxylate pyruvate to malate. Malate, isotopically labeled at the carboxyl can be prepared by carrying out the above reaction in bicarbonate buffer which is isotopically enriched at the carbons or oxygens. The NADPH used in the reduction may be regenerated as discussed previously (40). Alternatively, isotopically labeled pyruvate may be carboxylated using bicarbonate to yield oxaloacetate using a pyruvate carboxylase In the above embodiment used to generate citric acid cycle intermediates and isotopically labeled aspartate and glutamate, enzymatically catalyzed pathways exist other than those specifically mentioned which should be considered within the realm of the invention. For example, pyruvate may be converted to PEP by the pyruvate kinase catalyzed reaction. The PEP may then be carboxylated by PEP carboxylase or PEP carboxykinase to yield isotopically labeled oxaloacetate.

Oxaloacetate formed from pyruvate or L-alanine may be reduced also and go on to react with acetyl CoA to yield citrate in a citrate synthetase catalyzed reaction. The citrate so formed may be conveniently labeled at $C_1$ or $C_2$ by including in the reaction isotopically labeled acetate, CoA-SH and acetyl CoA synthetase. Hence the acetyl CoA involved in the citrate synthetase step is generated in situ. The isotopically labeled citrate product can be converted to isocitrate and on to α-ketoglutarate using aconitase and isocitrate dehydrogenase catalyzed reactions. In the present embodiment it is suggested that an NADP regeneration system other than the α-ketoglutarate/glutamate redox pair be used if one wishes to isolate α-ketoglutarate as a product. One possibility is a FMN/FMNH$_2$ redox pair. Other possibilities have been suggested (39). Preparation of citrate, isocitrate and α-ketoglutarate is indicated below.

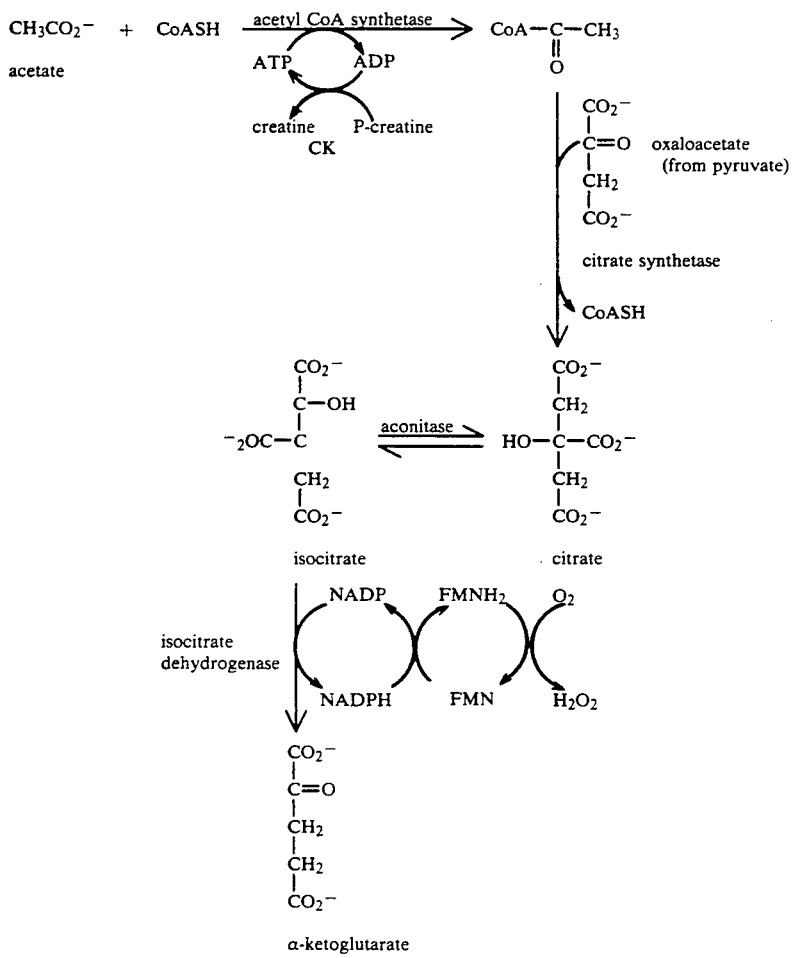

Preparation of L-Alanine, L-Aspartate, L-Glutamate and L-Glutamine

If glutamate dehydrogenase and ammonium ion are included in the reaction mixture, and NADP used in the second dehydrogenase step is regenerated and in so doing the product α-ketoglutarate is converted to glutamate. Hence, α-ketoglutarate remains in a low steady state concentration.

As discussed previously, some of the schemes used to prepare either FDP or some of the citric acid cycle intermediates may use either isotopically labeled pyruvate or L-alanine as a substrate. Hence, it is important to have a convenient route of preparing L-alanine. Labeled DL-lactate can be prepared chemically from propionic acid (24, 40). In this embodiment of the invention D- and L-lactate are oxidized to pyruvate using D- and L-lactate dehydrogenases. The NAD required in this reaction is regenerated with the reduction of α-ketoglutarate to glutamate (39). The glutamate so generated is used to transaminate the labeled pyruvate to alanine. In this final transaminase catalyzed reaction α-ketoglutarate is regenerated. Thus both the NAD and the glutamate/α-ketoglutarate may be kept in low steady-state concentrations. The enzyme catalyzed sequence of reactions used to prepare L-alanine from DL-lactic acid is shown below.

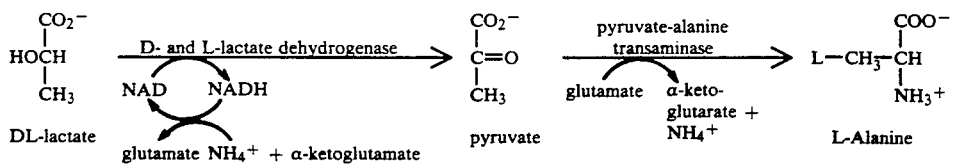

The preparation of citric acid cycle intermediates provides alternate routes for the preparation of isotopically labeled L-glutamic acid, L-glutamine and L-aspartate. For example, the pyruvate carboxylase catalyzed reaction yields oxalacetate as a product. If an excess amount of glutamate is included in the reaction mixture, aspartic acid labeled at any single position may be prepared via an oxaloacetate/pyruvate transaminase catalyzed reaction, as shown.

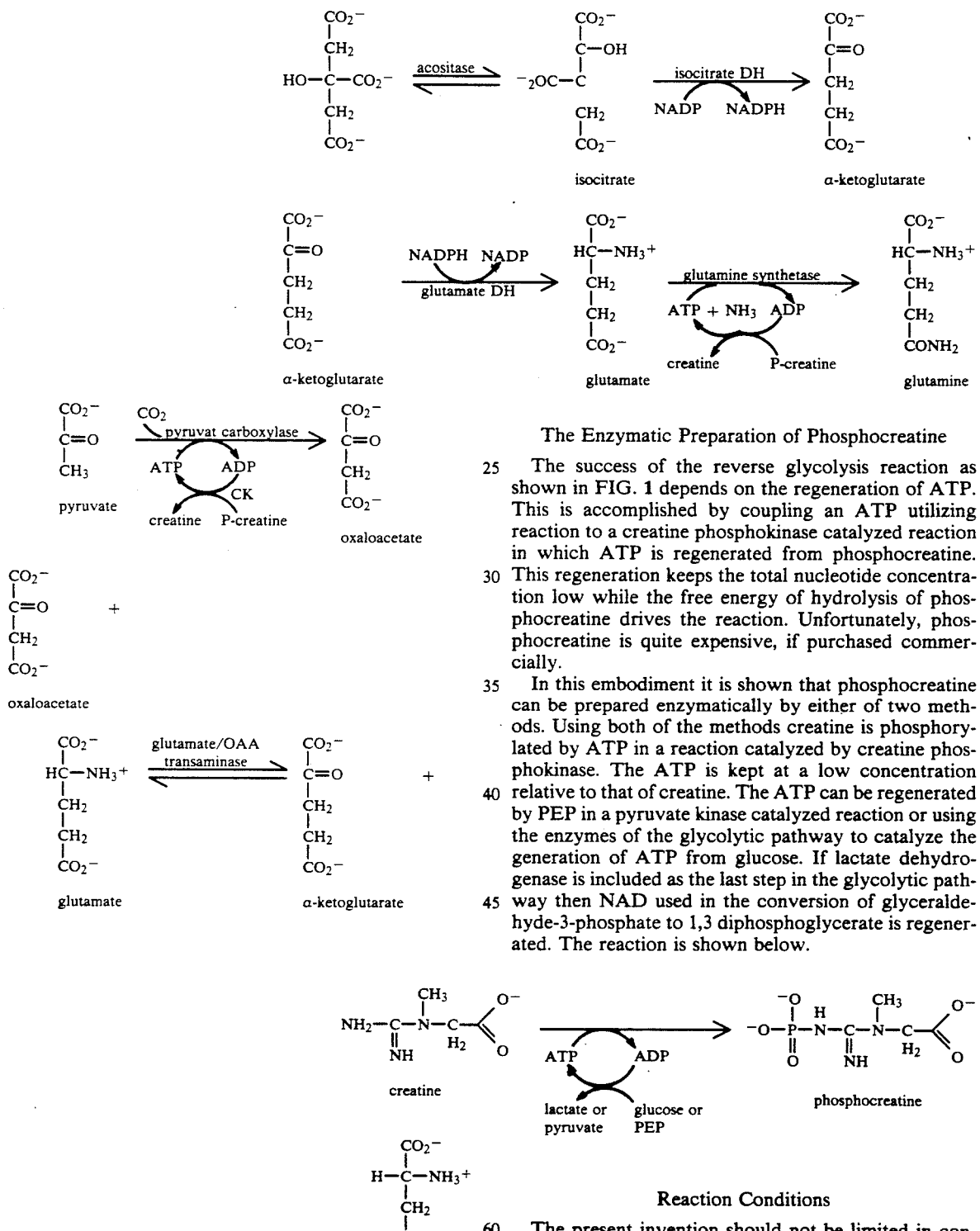

Furthermore, glutamine may be formed in an ensuing glutamine synthetase reaction.

The Enzymatic Preparation of Phosphocreatine

The success of the reverse glycolysis reaction as shown in FIG. 1 depends on the regeneration of ATP. This is accomplished by coupling an ATP utilizing reaction to a creatine phosphokinase catalyzed reaction in which ATP is regenerated from phosphocreatine. This regeneration keeps the total nucleotide concentration low while the free energy of hydrolysis of phosphocreatine drives the reaction. Unfortunately, phosphocreatine is quite expensive, if purchased commercially.

In this embodiment it is shown that phosphocreatine can be prepared enzymatically by either of two methods. Using both of the methods creatine is phosphorylated by ATP in a reaction catalyzed by creatine phosphokinase. The ATP is kept at a low concentration relative to that of creatine. The ATP can be regenerated by PEP in a pyruvate kinase catalyzed reaction or using the enzymes of the glycolytic pathway to catalyze the generation of ATP from glucose. If lactate dehydrogenase is included as the last step in the glycolytic pathway then NAD used in the conversion of glyceraldehyde-3-phosphate to 1,3 diphosphoglycerate is regenerated. The reaction is shown below.

The preparation of labeled α-ketoglutarate from pyruvate and acetic acid has been discussed. If one excludes FMN from the reaction medium and adds instead glutamate dehydrogenase and ammonium ion, labeled glutamate is obtained as the product, as shown below.

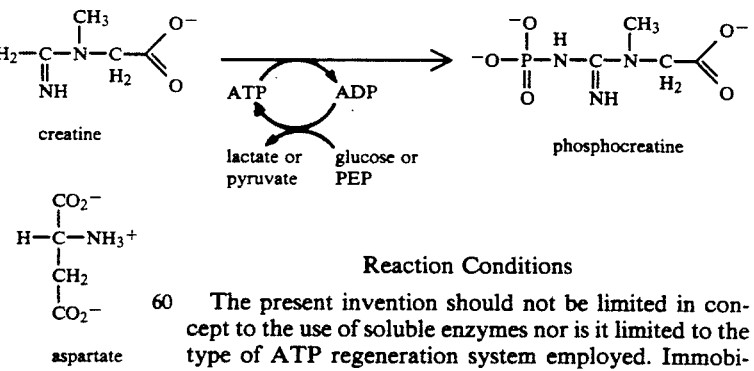

Reaction Conditions

The present invention should not be limited in concept to the use of soluble enzymes nor is it limited to the type of ATP regeneration system employed. Immobilized enzymes, for example, could be used.

It is also envisioned that the pH optimum for the reaction could be altered. As presently practiced, most of the soluble enzymes operate well in a neutral pH range. As a matter of practice a buffer is usually added to the reaction medium (generally 0.1M TRIS) in order to stabilize the pH. For some of the reactions described, a pH controller is used in order to keep the pH within a specified range. For example, this is the case for the reverse glycolysis reaction, where the overall absorption of a proton from the media in the 3-phosphoglycerate phosphokinase catalyzed step causes the pH of the reaction mixture to rise. Some or one of the enzymes used show enhanced activity in the presence of potassium or magnesium salts. For this reason potassium chloride and magnesium chloride are added to the medium as a matter of practice. It is recognized that the optimal pH and conditions can change if immobilized or custom synthesized enzymes are used. Use of such modified enzymes is contemplated within the scope of the invention.

While many of the reactions illustrated utilize enzymes of the glycolytic pathway, a variety of metabolic enzymes can be used to synthesize intermediates that can be either funnelled into the sequence leading from pyruvate to carbohydrate or used to prepare a labeled intermediate. For example, oxaloacetate decarboxylase may use labeled oxaloacetic acid as a substrate and produce as a product labeled pyruvate. This may then be converted to labeled fructose 1,6-diphosphate via the reverse glycolysis reaction shown in FIG. 1. Alternatively, labeled oxaloacetate may be converted to phosphoenolpyruvate via the phosphoenolpyruvate carboxykinase catalyzed reaction.

The concentrations of substrates used in the sample syntheses cited below are generally in the range of 0.05–0.1M. The enzyme concentrations are usually such as to produce a reasonable yield of product after an overnight incubation. It is realized that these concentrations may be varied and, as a result, may change the reaction yield and rate. Variation of such concentrations from those cited are thought to be within the scope of the present invention. It should be realized, however, that particularly the relative concentration of substrate to enzyme may have an allosteric effect on some of the enzymes, resulting in unexpected changes in reaction rates.

All of the enzymes which have been described above as catalyzing reactions for the preparation of carbohydrates, amino acids and citric acid cycle intermediates are available commercially. These enzymes are generally treated as off the shelf organic reagents and are not purified. If provided as suspensions in saturated ammonium sulfate solutions, these solutions are used directly, without dialysis.

In a preferred embodiment, all reactions are carried out in the presence of an inert atmosphere such as nitrogen or argon, and in the presence of a reduced sulfhydryl containing compound, such as mercaptoethanol. This has been found to preserve enzyme activity by preventing sulfhydryl group oxidation. Ethylenediaminetetraacetic acid (EDTA) is also added to the reaction medium in order to remove any effects of contaminating free metal ions. Since some of the reactions described are incubated for long periods of time at room temperature, there is an opportunity for growth of bacteria in the reaction medium. In order to prevent this sodium azide to 0.05% by weight is added.

The following examples illustrate preferred embodiments of the practice of the invention. Units of enzyme, as used in the examples, are defined as amount required to convert 1.0 μmole substrate to product per min at 37° C.

EXAMPLE 1

Enzymatic Conversion of Pyruvate to Fructose 1,6-Diphosphate 1.44 g of [2-$^{13}$C]sodium pyruvate (13.1 mmoles), 2.7 g of glucose (15 mmoles), 9.0 g of phosphocreatine (32 mmoles), and 0.360 g of disodium ATP and NADH (about 0.5 mmoles) were dissolved in 270 ml of an aqueous solution of 0.1M KCl, 2 mM ethylenediaminetetraacetic acid (EDTA), 2 mM mercaptoethanol, 10 mM MgCl$_2$ and 0.05% sodium azide. The pH of the solution was adjusted to 6.8. The mixture was placed in a sealed reaction vessel equipped with a pH electrode and a magnetic stir bar. To this mixture was added 2880 units of phosphocreatine phosphokinase (rabbit muscle), 5000 units of pyruvate kinase (rabbit muscle), 600 units of yeast enolase, 400 units of phosphoglycerate mutase (rabbit muscle), 600 units of phosphoglycerate kinase (rabbit muscle), 1440 units of glyceraldehyde-3-phosphate dehydrogenase (rabbit muscle), 20 units of glucose dehydrogenase, and 40 units of aldolase (rabbit muscle). (Triose phosphate isomerase was present as a contaminant of commercial phosphocreatine phosphokinase and enolase.) During the course of the reaction an argon purge was kept on the reaction vessel and the pH was controlled by addition of 1.0M HCl. The pH of the reaction mixture was maintained between 6.7 and 7.25. After 24 hours the enzymes were recovered by ultrafiltration. [2,5-$^{13}$C$_2$]fructose 1,6-diphosphate was then precipitated as its calcium salt by addition of a ten fold excess of CaCl$_2$. The overall yield of the reaction was in the range of 70–80%.

EXAMPLE 2

Enzymatic Conversion of L-Alanine to Fructose 1,6-Diphosphate $^{13}$C-labeled pyruvate can be prepared in situ as a substrate for the above reaction sequence from $^{13}$C-labeled L-alanine using the enzyme pyruvate-glutamate transaminase. 1.2 g of [3-$^{13}$C]L-alanine (13.1 mmoles) and 10.1 g of α-ketoglutarate (65.5 mmoles) were used as substrates in the reaction in place of sodium pyruvate. The reaction was carried out as previously described with the addition of 1000 units of pyruvate-glutamate transaminase. The overall yield (as determined by $^{13}$C NMR) was about 65%.

EXAMPLE 3

Preparation of Phosphocreatine

Two methods have been used to prepare phosphocreatine for its use in the ATP regeneration system described herein. Using both of these methods, creatine is phosphorylated by ATP using the enzyme phosphocreatine phosphokinase. The total concentration of ATP is kept low relative to the creatine concentration. ATP used in the reaction is regenerated using either glycolysis (Method A) or phosphoenolpyruvate and the enzyme pyruvate kinase (Method B).

Method A

The enzymes used in the preparation of phosphocreatine were dialyzed against 500 ml of 0.1M TRIS (6.05 g), 10 mM MgCl$_2$ (0.5 g), 2 mM EDTA (0.33 g), mercaptoethanol (70 μl) at pH 7.80. The enzymes were yeast hexokinase (35 units), phosphoglucose isomerase (25 units), phosphofructokinase (25 units), aldolase (27 units), phosphoglycerate kinase (71 units), phosphoglycerate kinase (71 units), phosphoglycerate mutase (31 units), lactic dehydrogenase (120 units), pyruvate kinase (50 units), enolase (90 units), creatine phosphokinase (175 units), and glyceraldehyde phosphate dehydrogenase (90 units). Dialysis time was approximately 1 hour. The reaction mixture consisted of 10 mmoles of sodium pyruvate 10 mmoles of potassium phosphate, 5 mmoles glucose, 0.18 mmoles at ATP, 0.18 mmoles of NAD and 18 mmoles of creatine dissolved in 200 ml of 0.1M TRIS, 10 mM $MgCl_2$, 2 mM EDTA and 2 mM mercaptoethanol. This mixture also contained 0.05% $NaN_3$ in order to inhibit bacterial growth. Prior to addition of the dialyzed enzymes, the reaction mixture was titrated to pH 8.0 and purged for 15 min with argon gas. The dialyzed enzymes were then added to the solution. The reaction was carried out under argon and the pH of the solution was maintained between 7.7 and 7.9 with a pH controller by adding 1N NaOH to the reaction mixture when the pH dropped below 7.7. The final yield of the reaction mixture as shown by $^{31}P$ nuclear magnetic resonance spectrum was 84% phosphocreatine. After 2 days, the barium salt of the phosphocreatine was formed by adding 2.0 g of $BaCl_2$ to the reaction mixture. Suction filtration of the solution yielded 8.32 g of the barium salt. The phosphocreatine barium salt was then converted to the sodium salt and fractionally crystallized from aqueous ethanol (41). Fractional crystallization yielded 1.70 g of sodium phosphocreatine.

Method B

To 100 ml of 0.1M KCl, 10 mM $MgCl_2$, 2 mM EDTA and 2 mM mercaptoethanol was added 1.02 g phosphoenolpyruvate (monopotassium salt), 1.0 g creatine and 60 mg ATP. The mixture was stirred and the pH adjusted to 7.5. Undialyzed pyruvate kinase (20 units) and creatine phosphokinase (80 units) were then added to the reaction mixture. The reaction was carried out for 2 days under ambient conditions. The pH of the reaction mixture was found to be 7.1–7.4 after this period of time. The final yield as shown by $^{31}P$ nuclear magnetic resonance was 95% phosphocreatine. Suction filtration yielded 2.20 g of the barium salt. Fractional crystallization from aqueous ethanol yielded 1.04 g of sodium phosphocreatine.

EXAMPLE 4

Enzymatic Preparation of $^{13}C$-Ribose Nucleotides

The calcium salt of $^{13}C$-labeled FDP prepared according to Example 1 was dissolved in water and treated with a molar excess of Dowex-50 (hydrogen form). The resin was removed and concentrated HCl was added to the solution until the final hydrogen ion concentration was approximately 1M. The solution was then incubated in a water bath at 80° C. for five hours. This solution was cooled and neutralized. The product, $^{13}C$-fructose-6-phosphate, can be isolated as its barium salt and recrystallized as its sodium salt (42). The product can then be converted to $^{13}C$-ribose-5-phosphate and the respectively labeled nucleotide using known procedures (14–15,37–39).

EXAMPLE 5

Preparation of 3-$^{13}C$ Malate

Method A 3 ml of a solution containing 50 mM [2-$^{13}C$] pyruvate (sodium salt) 0.2M sodium bicarbonate, 2 mM ATP, 2 mM NADH, 50 mM phosphocreatine, 50 mM glucose-6-phosphate, 10 mM $MgCl_2$, 2 mM mercaptoethanol, 2 mM EDTA in 0.1M TRIS was adjusted to pH 7.5. To this was added 1.2 units of phosphoenolpyruvate carboxylase (corn), 150 units of creatine phosphokinase, 10 units of malic dehydrogenase, 10 units of glucose-6-phosphate dehydrogenase (Leuconostoc mesenterocides) and 500 units of pyruvate kinase. After an overnight incubation [3-$^{13}C$] malate was isolated by anion exchange chromatography using an acetic acid gradient (14–15). The yield was about 40%.

Method B 3 ml of a solution containing 50 mM pyruvate, 2 mM NADP, 50 mM glucose-6-phosphate, 0.2M sodium bicarbonate, 10 mM $MgCl_2$, 2 mM mercaptoethanol and 2 mM EDTA was adjusted to pH 7.0. To this solution was added 10 units of malic enzyme and 10 units of glucose-6-phosphate dehydrogenase. After overnight incubation the yield of [3-$^{13}C$] malate was assessed by $^{13}C$ MNR to be about 85%.

Method C

To a 3 ml solution containing 50 mM [2-$^{13}C$]pyruvate, 50 mM phosphocreatine, 2 mM ATP, 2 mM NADH (or NAD), 50 mM glucose-6-phosphate, 10 mM sodium acetate, 0.2M sodium bicarbonate, 2 mM mercaptoethanol, 2 mM EDTA and 0.1 mM coenzyme A (CoA), pH 7.5, was added 2 units pyruvate carboxylase, 10 units of malic dehydrogenase, 10 units of acetyl coenzyme A synthetase and 10 units of glucose-6-phosphate dehydrogenase. Following overnight incubation, the yield of [3-$^{13}C$]malate was assessed by $^{13}C$ NMR to be about 80%.

EXAMPLE 6

Preparation of [3,4,5-$^{13}C_3$]Citrate and [3-$^{13}C$]Citrate

The pH of 3 ml of a solution containing 0.1M TRIS, 0.2M sodium bicarbonate, 10 mM $MgCl_2$, 2 mM mercaptoethanol, 2 mM EDTA, 50 mM [2-$^{13}C$]pyruvate (sodium salt), 50 mM [1,2-$^{13}C_2$]sodium acetate, 0.1 mM CoA, 2 mM ATP and 0.1M phosphocreatine was adjusted to 7.6. To this solution was added 4 units of citrate synthase, 300 units of creatine phosphokinase, 2 units of pyruvate carboxylase, 10 units of acetyl coenzyme A synthetase and 41 units of myokinase. Following an overnight incubation, the yield of product was determined to be about 60% by $^{13}C$ NMR. [3-$^{13}C$]citrate was produced with equal yield by running the same reaction using unlabeled acetate in place of [1,2-$^{13}C_2$]acetate.

EXAMPLE 7

Preparation of [2-$^{13}C$]L-Alanine from [2-$^{13}C$]DL-Lactate 27 mg of [2-$^{13}C$]DL-lactate (0.33 mmoles), 44 mg of glutamic acid (0.03 mmoles) and 7 mg of NAD (0.01 mmoles) were dissolved in 3 ml of 0.1M Tris buffer containing 10 mM $MgCl_2$, pH 7.5. To this was added 200 units of L-lactate dehydrogenase and D-lactate dehydrogenase, 200 units of L-glutamate dehydrogenase (in 0.5 ml of saturated $(NH_4)_2SO_4$ and 100 units of pyruvate-glutamate transaminase (in 0.1 ml of saturated $(NH_4)_2SO_4$). Within 72 hours at room temperature nearly all of the [2-$^{13}C$]L-lactate had been converted to [2-$^{13}C$]L-alanine. The yield as judged by $^{13}C$ NMR was about 80%.

EXAMPLE 8

Preparation of [2-$^{13}$C]Aspartate from [2-$^{13}$C]Pyruvate

The pH of 3 ml of solution containing 0.1M TRIS, 0.2M sodium bicarbonate, 0.1M sodium glutamate, 10 mM MgCl$_2$, 2 mM mercaptoethanol, 2 mM EDTA, 50 mM [2-$^{13}$C]pyruvate, 2 mM ATP, 50 mM phosphocreatine, 0.1 mM CoA and 50 mM sodium acetate was adjusted to 7.5. To this solution was added 300 units of creatine phosphokinase, 2 units of pyruvate carboxylase, 41 units of myokinase, 10 units of acetyl coenzyme A synthetase and 20 units of glutamic-oxalacetic transaminase. Following an overnight incubation, the yield of [2-$^{13}$C]aspartic acid from pyruvate was 45%, as determined by $^{13}$C NMR.

EXAMPLE 9

Preparation of [2-$^{13}$C]L-Alanine, [3-$^{13}$C]α-Ketoglutarate and [3-$^{13}$C]L-Glutamate from [2-$^{13}$C]Pyruvate

[3-$^{13}$C]Citrate was prepared according to Example 6. To this reaction mixture was added 2 units of aconitase, preincubated with a Fe$^{+2}$/cysteine mixture in order to preserve enzyme activity (42), 24 units of glutamate dehydrogenase and 4 units of isocitrate dehydrogenase. Glutamate/pyruvate transaminase was present in the commercial preparations of enzymes added to the reaction mixture. The solution was then made 2 mM in NADP and the pH adjusted to 7.5. Following an overnight incubation, the final reaction mixture contained about 40% [3-$^{13}$C]L-glutamate, 20% [2-$^{13}$C]L-alanine and 20% [3-$^{13}$C] α-ketoglutarate, as determined by $^{13}$C NMR. The products could be separated using anion exchange chromatography (14–15).

The present invention has been described in terms of particular embodiments found by the inventor to comprise preferred modes of practice of the invention. It will be appreciated by those of skill in the art that in light of the present disclosure numerous modifications and changes can be made in the particular embodiments exemplified without departing from the intended scope of the invention. For example, functionally equivalent enzymes or stabilized active fragments of glycolytic cycle enzymes could be employed without affecting the intended nature and practice of the invention. All such modifications are intended to be included within the scope of the claims.

REFERENCES

The references listed below are incorporated herein by reference to the extent they supplement, explain, provide a background for or teach methodology, techniques and/or compositions employed herein.

1. Barker, R. and Serrianni, A. S., Acc. Chem. Res., 19, 307–313 (1986).
2. Serianni, A. S., Nunez, H. A., Hayes, M. L. and Barker, R., Meth. Enzymol., 89, 64 (1982).
3. Serianni, A. S. and Barker, R., "Synthetic Approaches to Carbohydrates Enriched with Stable Isotopes of Carbon, Hydrogen and Oxygen," In Isotopes in the Physical and Biomedical Sciences, (Eds., Jones, J., Buncel, E.), Elsevier, Amsterdam; and references cited therein.
4. Angyal, S. J., Stevens, J. D. and Odier, L., Carbohydr. Res., 157, 83–94 (1986).
   Clark, E. L. and Barker, R., Carbohydrate Res. 153, 253–261 (1986).
6. Bhattacharjee, S. S., Schwarcz, J. A. and Perlin, A. S., Carbohydr. Res., 42, 259–266 (1975).
7. Kim, M.-J., Hennen, W. J., Sweers, H. M. and Wong, C.-H., J. Am. Chem. Soc., 110, 6481–6486 (1988).
8. Bednarski, M. D., Simon, E. S., Bischofberger, N., Fessner, W.-D., Kim M.-J., Lees, W., Saito, T., Waldmann, H. and Whitesides, G. M., J. Am. Chem. Soc., 111, 627–635 (1989).
9. Durrwachter, J. R. and Wong, C.-H., J. Org. Chem., 53, 4175–4181 (1988).
10. Wong, C.-H. and Whitesides, G. M., J. Org. Chem., 48, 3199–3205 (1983).
11. Bednarski, M. D., Saldmann, H. J. and Whitesides, G. M., Tetrahedron Lett., 48, 5807–5810 (1986).
12. Borysenko, C. W., Spaltenstein, A., Staub, J. A. and Whitesides, G. M., J. Am. Chem. Soc., 111, 9275–9276 (1989).
13. Durrwachter, J. R., Drueckhammer, D. G., Nozaki, K., Sweers, H. M. and Wong, C.-H. J. Am. Chem. Soc. 108, 7812–7818 (1986).
14. U.S. Pat. No. 4,656,133, Goux, Apr. 17, 1987.
15. Goux, W. J., Carbohydr. Res., 122, 332–339 (1983).
16. Kerr, V. N. and Ott, D. G., J. Label. Comp. Radiopharm., 15, 603–609.
17. Kendall, E. C. and McKenzie, B. F., Org. Syn. Coll., 2, 491–194 (1943).
18. Loftfield, R. B. and Eigner, E. A., Biochem. Biophys. Acta, 130, 449–457 (1966).
19. Berger, A., Smolarsky, M., Kurn, N., and Bosshard, H. R., J. Org. Chem., 38, 457–460 (1973).
20. Baddiley, J., Ehrensvard, C., and Nilsson, H., J. Biol. Chem., 178, 399–402 (1949).
21. Fryzuk, M. D. and Bosnich, B., J. Am. Chem. Soc., 99, 6262–6267 (1977).
22. Giza, Y. H., and Ressler, C., J. Labelled Compd., 5, 142–151 (1969)
23. Havranek, M., Kopecka-Schadtova, H., and Veres, K., J. Labelled Compd., 6, 345–354 (1970).
24. LeMaster, D. M. and Cronan, J. E., Jr., J. Biol. Chem., 257, 1224–1230.
25. Ott, D. G. "Synthesis with Stable Isotopes of Carbon, Nitrogen and Oxygen," John Wiley, N.Y., N.Y., 1982, pp. 63–66.
26. Baldwin, J. E., Dyer, R. L., Ng, S. C., Pratt, A. J., and Russell, M. A., Tet. Lett., 28, 3745–3746 (1987).
27. Wood, T. B., Weisz, O. A., Kozarich, J. W., J. Am. Chem. Soc., 106, 2222–2223 (1984).
28. Malloy, C. R., Sherry, A. D., and Jefferey, F. M. H., J. Biol. Chem., 263, 6964–6971 (1988).
29. Katz, J., Lee, W.-N. P., Wals, P. A., Bergner, E. A., J. Biol. Chem,. 264, 12994–13001 (1989).
30. Schulman, G. I., Alger, J. R., Prichard, J. W., J. Clin. Invest., 74, 1127 (1984).
31. Kazlauskas, R. J. and Whitesides, G. M., J. Org. Chem., 50, 1069–1076 (1985).
32. Hirschbein, B. L., Mazenod, F. P. and Whitesides, G. M., J. Org. Chem., 47, 3765–3766 (1982).
33. Crans, D. and Whitesides, G. M., J. Org. Chem., 48, 3130–3132 (1983).
34. Simon, E. S., Grabowski, S. and Whitesides, G. M., J. Org. Chem., 55, 1834–1841 (1990).
35. Wong, C.-H. and Whitesides, G. M., J. Am. Chem. Soc., 103, 4890–4899 (1981).
36. Hartman, F. C., J. Am. Chem. Soc., 92, 2170–2173 (1970).
37. Gross, A., Abril, O., A., Lewis, J. M., Geresh, S. and Whitesides, G. M., J. Am. Chem. Soc., 105, 7428–7435 (1983).

38. Walt, D. R., Findeis, M. A., Rio-Mercadillo, V. M., Auge, J. and Whitesides, G. M., J. Am. Chem. Soc., 106, 234–239 (1984).
39. Lee, L. G. and Whitesides, G. M., J. Am. Chem. Soc., 107, 6999–7008 (1985).
40. Ott, D. "Synthesis with Stable Isotopes," John Wiley, New York, N.Y. (1981), p. 47.
41. A. H. Ennor and L. A. Stocken, Biochemical Preparations, 5, 9.
42. Fansler, B. and Lowenstein., J. M., Methods in Enzymology (ed. S. P. Colowick and N. O. Kaplan), V. 13, p. 26 (1969).

What is claimed is:

1. A method of preparing [L-glutamatic] L-glutamic acid isotopically labeled at carbon-3 or carbons 3,4,5 comprising incubating istopically labeled citrate or citrate and nonistopically labeled L-alanine with aconitase, isocitrate dehydrogenase, L-glutamate dehydrogenase, L-glutamate/pyruvate transaminase, and a nicotine nucleotide phosphate regeneration system for a time sufficient to convert the labeled citrate to isotopically labeled glutamic acid in yields of at least 40%.

2. The method of claim 1 wherein the nicotine adenine dinucleotide regeneration system comprises nonisotopically labeled pyruvate, a nicotinamide adenine nucleotide phosphate and lactic dehydrogenase.

3. The method of claim 1 wherein the nicotine adenine phosphate regeneration system comprises flavin mononucleotide.

4. The method of claim 1 wherein the nicotine nucleotide phosphate is about 2% to about 5% of the level of isotopically carbon-labeled citrate present during the incubating.

* * * * *

UNITED STATES PATENT AND TRADEMARK OFFICE
CERTIFICATE OF CORRECTION

PATENT NO. : 5,227,296
DATED : July 13, 1993
INVENTOR(S) : Warren Goux

It is certified that error appears in the above-indentified patent and that said Letters Patent is hereby corrected as shown below:

In column 21, line 14, delete "[L glutamatic].

In column 21, line 16, insert --C-$^{13}$C-- after "labeled".

In column 21, line 16, insert --3,4,5-$^{13}$C-- after "or".

Signed and Sealed this

Twenty-sixth Day of July, 1994

Attest:

BRUCE LEHMAN

Attesting Officer

Commissioner of Patents and Trademarks